United States Patent [19]

Lusas et al.

[11] Patent Number: 5,300,312
[45] Date of Patent: Apr. 5, 1994

[54] A METHOD OF PREPARING READY-TO-EAT INTERMEDIATE MOISTURE FOODSTUFFS

[75] Inventors: Edmund W. Lusas, Bryan; Gabriel J. Guzman, College Station; Steven C. Doty, Caldwell, all of Tex.

[73] Assignee: Texas A&M University, College Station, Tex.

[21] Appl. No.: 999,562

[22] Filed: Dec. 30, 1992

Related U.S. Application Data

[63] Continuation of Ser. No. 732,664, Jul. 19, 1991, abandoned.

[51] Int. Cl.$^5$ .............................................. A23L 1/20
[52] U.S. Cl. ................................. 426/634; 426/516; 426/574; 426/629; 426/641; 426/656; 426/802
[58] Field of Search .............. 426/802, 656, 634, 516, 426/104, 445, 448, 512, 513, 516–519, 623, 630, 641, 644, 646, 647, 805, 810, 574, 629, 600

[56] References Cited

U.S. PATENT DOCUMENTS 3,745,021 7/1973 Van Middlesworth et al.
4,039,691 8/1977 Hildebolt ............................ 426/656
4,061,784 12/1977 Youngquist ......................... 426/802
4,133,897 1/1979 Flanyak et al. .................... 426/802
4,185,123 1/1980 Wenger et al. ..................... 426/516
4,332,823 1/1982 Buemi ................................ 426/802
4,358,468 11/1982 Dolan et al. ....................... 426/802
4,369,195 1/1983 Nelson et al. ...................... 426/656
4,376,134 3/1983 Kumar ................................ 426/802
4,910,038 3/1990 Ducharme .......................... 426/516
5,000,973 3/1991 Scaglione et al. ................. 426/549
5,026,572 6/1991 Neiberger .......................... 426/516

*Primary Examiner*—Donald E. Czaja
*Assistant Examiner*—Leslie Wong
*Attorney, Agent, or Firm*—Cox & Smith Incorporated

[57] ABSTRACT

A method of producing a ready-to-eat intermediate-moisture texturized protein foodstuff which simulates meat and has an extended shelf life comprises pretexturizing a vegetable protein source with a first source of water such as meat, meat by-products or other liquids by cooking/extrusion, combining the texturized fraction with other ingredients in a second cooking/extrusion step, and pasteurizing the final mixture. Shelf stability is achieved through control of free water content and activity in the product.

10 Claims, No Drawings

A METHOD OF PREPARING READY-TO-EAT INTERMEDIATE MOISTURE FOODSTUFFS

This application is a continuation of application Ser. No. 07/732,664 filed on Jul. 19, 1991 now abandoned.

BACKGROUND OF THE INVENTION

1. Field of the Invention

This invention relates to a method of processing vegetable protein and other ingredients optionally adding meat or meat by-products to produce intermediate moisture foodstuffs which simulate animal meat products in appearance, flavor, texture and taste. This invention also relates to a method comprising a series of extrusion cooking steps for producing the intermediate moisture foodstuffs described herein. These vegetable or vegetable/meat foodstuffs have prolonged shelf lives which make them suitable for human consumption that may be sold as a snack or high protein supplement without need for refrigeration.

2. Description of the Background

Animal protein is generally less abundant and more expensive than vegetable protein. It has been estimated that ten pounds of vegetable protein feed are required to feed the animal source for every pound of animal protein produced. It, therefore, makes economic sense to utilize vegetable rather than animal protein for the commercial preparation of foodstuffs.

Animal protein is prized for its flavor and its desirable nutritional balance of dietary essential amino acids. Its utilization, however, has disadvantages such as the fact that it is more expensive and generally less abundant than vegetable protein. It is thus desirable to substitute vegetable for animal protein whenever possible or to at least "extend" the use of animal protein by mixing in vegetable protein components and other ingredients. Examples of a vegetable protein source are soy and other oilseeds proteins, which are used in this invention to produce a meat-like texture product. Moreover, animal protein becomes denatured at approximately 170°-180° F. and cannot be reshaped at the higher temperatures which are needed to pasteurize microorganisms, whereas, such temperatures and higher may be used on the vegetable protein sources. In addition, the incorporation of vegetable protein influences the shelf life of an edible product.

Recent trends in food consumption also show that people are becoming more health conscious and monitoring their food intake as the result of recent research into the possible effects of particular foodstuffs on health. Animal products are the only dietary source of cholesterol and may contain high levels of saturated fats. This has led large numbers of health professionals to recommend that the public significantly reduce their intake of red meats Fish and poultry have become popular substitutes, but vegetable protein also is increasing in popularity. Generally, vegetable protein is eaten in the form of beans or other natural products alone or mixed with animal foodstuffs, but enriched sources such as flours, concentrates and isolates of defatted oilseed, especially soy, have been developed for use as food ingredients.

The term "intermediate moisture food", as used in the present patent defines a food that is flexible, easy to masticate, and does not produce dryness to the mouth while at the same time being resistant to microbial growth. In general, the foodstuffs falling under this category have a water content of about 15 to 40 wt %, and more preferably about 20 to 30 wt %.

Techniques for extending meat, meat by-products and/or trimmings with vegetable protein are known in the art.

U.S. Pat. No. 3,745,021 to Van Middlesworth et al. describes a method of making intermediate moisture pet foods using an extrusion/expansion technique. Meat trimmings are combined with 6–12 wt % water and a 3–25 wt % farinaceous material containing almost equal parts of wheat gluten/soy flour and starchy materials to produce a bubbly-textured non-fibrous end-product. Starchy materials disclosed are corn, wheat, barley and derivatives thereof. Intermediate moisture products are said to be achieved with water-soluble sugars that are added to the final product to raise its osmotic pressure. The high osmotic pressure created by the sugar is said to limit the amount of unbound water available to support microbiological growth.

U.S. Pat. No. 4,358,468 to Dolan et al. discloses a method of co-extruding vegetable proteins simulating red-meat and white-fat phases in an extruder to produce a pet food which resembles lean meat marbled with fat. Intermediate moisture levels are achieved in the above product with unspecified aqueous solutes. This prior art process casts and commingles homogenous red and white melts and results in a non-structured marbled product. It does not, however, produce entirely or partially striated fractions that resemble meat.

The above-described methods are primarily directed at making intermediate moisture foods for domestic pets that resemble the appearance of meat without actually having the various characteristics of meat.

A principal problem preventing long-term storage of ready-to-eat foodstuffs is the growth of microorganisms in a medium rich in nutrients. The growth of microorganisms, especially bacteria, is closely associated with the availability of free water in the foodstuff. The water available to microorganisms in a food product may be defined as the equilibrium relative humidity of the product rather than the weight percentage of water of the product. Yeast and molds, for example, are particularly effective in obtaining water even under lower water activity conditions than for bacteria. It is therefore of extreme importance for the successful production of a ready-to-eat product to significantly reduce the growth of microorganisms so that the foodstuff is shelf stable and can be stored for prolonged periods of time for retail sale.

Up to the present time, it has been a general practice to include additional food-grade chemical preservatives to prevent the growth of microorganisms in intermediate moisture foodstuffs.

An alternative method to retard microbial growth is the reduction of available moisture in the product. One method of achieving almost complete reduction of moisture is by dehydration. Dehydrated foods, however, have poor taste and texture, and must be rehydrated prior to consumption to make them palatable. It is, therefore, highly desirable that the processed food product have sufficient moisture to be palatable while keeping the microbial count low to prevent spoilage.

Thus, there still exists a need for a vegetable food product that resembles meat, is shelf stable and has an agreeable texture and feel to the mouth.

SUMMARY OF THE INVENTION

This invention relates to a method of preparing a ready-to-eat, intermediate moisture meat-like foodstuff, that comprises admixing a vegetable protein source selected from the group consisting of a dehulled, oilseed protein meal, flour, concentrate and isolate with a first source of water to a moisture content of about 25-50 wt %;

cooking, working and extruding the mixture at a temperature of about 212°-350° F. and an exit pressure of about 200-2000 psi to produce a texturized foodstuff;

optionally shredding the texturized product into shreds of a desired size and shape;

mixing the texturized shreds with a second source of water, sugars, flours, preservatives and other additives;

pasteurizing the product by heating to over about 190° F. in a cooker extruder decreasing the temperature of the pasteurized foodstuff to about ambient temperature; and shaping and cutting the heated foodstuff to a desired shape and size and sealing in an appropriate packaging material.

This invention also relates to a foodstuff prepared by the method of the invention described above. The foodstuff may be in a form such as a bar, stick, paste, loaf and/or pie, and it may further contain other components such as a liquid protein concentrate, and additives such as colorants, texturizers, fillers, flavorings, and the like, as well as dry fruit pieces, nuts, seeds and the like.

Other objects, advantages and features of the present invention will become apparent to those skilled in the art from the following discussion.

DESCRIPTION OF THE PREFERRED EMBODIMENTS

The present invention arose from a desire by the inventors to provide an improved foodstuff of intermediate moisture that has prolonged shelf life, and low animal protein and fat content as well as a taste, texture and appearance that closely resemble animal meat.

The method of the invention produces foods having a prolonged shelf life by controlling the free water content of the foodstuff, thereby preventing the growth of microorganisms.

The present invention provides a method of preparing an intermediate moisture foodstuff, that comprises admixing a vegetable protein source selected from the group consisting of a dehulled, oil seed protein meal, flour, concentrate and isolate with a first source of water to a moisture content of about 25-50 wt %;

cooking and extruding the mixture at a temperature of about 212°-350° F. and an exit pressure of about 200-2000 psi to produce a texturized foodstuff;

optionally shredding the extruded material into shreds of a desired size and shape;

mixing the texturized shreds with a second water source, sugars, salts, flavors, colors, preservatives and other cereals and/or oilseed ingredients;

pasteurizing by extrusion cooking the mix at above about 190° F. and up to about 350° F.;

decreasing the temperature of the texturized foodstuff to about ambient temperature; and shaping and cutting the texturized foodstuff to a desired shape and size.

The vegetable protein source in the present method may be mixed with other components lacking animal protein, whereby a totally vegetarian product is obtained, or with an animal meat source.

Another type of product encompassed herein is a meat-flavored vegetable protein foodstuff, where the meat flavor is provided by finely ground meat or a liquid protein digest or extract such as a meat sauce or broth. The liquid protein digest or extract is generally one where the meat is degraded, e.g., by the effect of a proteolytic enzyme, and then optionally homogenized.

In, general, an oil source may be added to the mixture, before the second extrusion step, to improve its consistency as well as its taste. However, the mixture may be prepared without oil or fat, as well.

In addition to dehulled oilseed protein meals, flours, concentrates and isolates and the source of water, other ingredients such as salts, colorings, antioxidants, antimicrobial agents, plant source fibers and starchy ingredients may also be incorporated at this stage.

Both extrusion steps of the method of the invention may be conducted on a single extrusion machine or with a double or twin extrusion machine.

In one particular embodiment of the invention one or more extrusion steps may be conducted as disclosed in U.S. patent application Ser. No. 07/670,007 by the same inventors, filed on Mar. 15, 1991, now abandoned and refiled as a continuation, U.S. patent application Ser. No. 07/852,835 entitled "NON-POROUS, VEGETABLE PROTEIN FIBER PRODUCTS AND METHODS OF MAKING AND USING". Portions of that application pertinent to the description and enablement of the preparation of the proteinaceous fibers is incorporated herein by reference.

The combination of extrusion-textured ingredients, texturizing, other additives, short-term high temperature heating, and the optional incorporation of antimicrobial ingredients result in a ready-to-eat, intermediate moisture, shelf-stable product such as the one disclosed herein.

The method of the invention extrudes a vegetable protein source or a combination of vegetable and animal protein sources under temperature and pressure sufficient to texturize the protein. Throughout these steps, the temperature is maintained at a range that does not denature the protein.

Towards the end of the first extrusion step, however, the temperature may be rapidly increased and then rapidly lowered to obtain the desired texture while retaining the nutritional value of the foodstuff. The resulting extrusion-texturized particles may be ground to shreds of a desired size and shape. The texturized ingredients are then mixed with additional source of water and other components, and pasteurized at about 190° F. or up to about 350° F., in a second cooking extrusion step. The extrusion steps may be conducted by placing the mixture in an extruder at a temperature that is rapidly raised to about 212°-350° F., and more preferably about 218°-330° F., and an exit pressure of about 200-2000 psi, and more preferably about 500-1000 psi, to produce a texturized foodstuff. The temperature and pressure may be varied to adapt to different types of materials utilized.

As already disclosed, the microbiological spoilage of food involves the multiplication of existing yeast, mold and bacteria over a period of time. An initial reduction in the number of microorganisms will, therefore, minimize the extent of any future microbial proliferation. Following the second pasteurization, the total water content is generally reduced to a range of about 20 to 30 wt %.

The texturized vegetable protein may optionally be blended with a number of ingredients, such as flavor and color enhancing ingredients, preservatives, sweeteners, salts, fillers, bulking agents, edible acids, antioxidants, emulsifiers, oils or fats, polyalcohols, and additional ingredients depending on the desired characteristics of the end product. The amounts and types of these additives are particularly tailored to the product, and an artisan would know how to determine them from the teachings of the art. For example, a sweet protein product may require a lesser amount of salt and a higher amount of a sweetener, and vice versa, a non-sweet type of product would have a smaller amount of sweetener and a higher content of salt and/or oils or fats, and the like. Colorings, preservatives, antioxidants, emulsifiers, anti-browning agents, polyalcohols, fillers and bulking agents are known in the art and so are the amounts in which they are used in an edible product. A requirement of these additives is that they be edible and that they do not interfere with the pleasant flavor, feel and consistency of the foodstuff.

The overall mixture may then be put through a second extrusion step. The doubly extruded product may then be further processed and packaged.

The control of water activity in the resulting foodstuff product is at the core of the present invention which produces preservable foods having extended shelf lives. Water activity is defined as the amount of unbound, free water in a system available to support biological and chemical reactions (Potter, Food Science, 4th Ed., p.296, AVI Pub. Co., Wesport, Conn. (1986)).

Water activity is a concept that differs from that of absolute water content of a particular food. In fact, some foods may have high levels of total water content while at the same time possess low water activity. Water activity, $A_w$, may be defined as the ratio between the vapor pressure of water in a food, VP, to the vapor pressure of pure water, VPo, at room temperature and a specified atmospheric pressure (Desrosier, The Technology of Food Preservation, 4th Ed., p.291, AVI Pub. Co., Wesport, Conn. (1977)).

$$A_w = VP/VPo$$

This ratio provides the amount of free water present in the food expressed as the equilibrium state of the unbound water content in relation to the vapor pressure of the surrounding environment in which the food is stored, under conditions of room temperature and atmospheric pressure.

Ideally, an intermediate moisture food product will have a low Aw value, yet have a high total bound-moisture content. Excessive free water is thus reduced to prevent microbial proliferation while enough bound water is provided to make the storeable foods moist and palatable. Most bacterial growth is adequately inhibited at relatively high Aw values. However, most molds are resistant to lower $A_w$ conditions and, therefore, antymicotics such as potassium sorbate are generally added to control their growth.

Although values outside of this range are also encompassed herein, a preferred $A_w$ range for the present foodstuff is about 0.60 to 0.95, and more preferably about 0.70 to 0.90.

Water activity is affected by the amount of water (solvent) present in the product, and the competition for that water by all solutes as indicated by the colligative property of osmotic pressure. Water activity may be estimated as the decimal mole fraction of the solvent (water) molecules compared to all (disassociated and non-disassociated) solute and solvent molecules in the product. Salts are some of the most effective ingredients per unit weight to increase osmotic pressure and decrease water activity since they have low molecular weights and often dissociate into two or more ions, each of which contributes to the osmotic pressure as a short-chain molecule dissolved therein. The relative effectiveness of molecules in reducing water activity per gram of solute decreases as their molecular size increases. Similarly,, this also occurs when going from dissociated salts to polyhydroxyl compounds containing 3C-compounds like glycerol and propylene glycol, to 6C-compounds like dextrose, fructose and sorbitol, to 12C-compounds like sucrose and maltose or small polymers like dextrins or solubilized starches and proteins. Products having pHs of 5.5 or lower discourage the growth of bacteria and enhance solubility of antimicrobial compounds such as potassium sorbate. If, e.g., citric acid, is used as an acidulant, the product also has a citrus-like flavor. Propylene glycol, also has a microbe-inhibiting effect in addition to increasing osmotic pressure.

The water source utilized in blending with the vegetable protein source is generally selected from meats such as beef, pork, lamb, chicken, turkey, fish, seafood, and the like, a liquid meat extract such as meat gravy, broth, and the like, a flour dough such as that produced by the blending of various vegetable flours, and other ingredients such as milk, buttermilk, cheese whey, beer, diluted cereal grain extracts, and fresh fruits and vegetables.

In a preferred embodiment of the invention, the water source is meat and the meat is reduced into pieces prior to its admixing with a vegetable protein source. The meat may be ground, chopped, and the like, in order to reduce its size and shape, as is known in the art.

In another particularly preferred embodiment of the invention, the method further comprises blending the texturized foodstuff with the liquid meat extract described above in a proportion of about 15–40 wt % to about 20–50 wt % prior to the pasteurizing and second extrusion step, and still more preferably the proportion is about 20–30 wt % of the texturized foodstuff to about 30–40 wt % of the liquid meat extract. Still more preferred is blending a liquid meat extract such as a beef gravy obtained by the proteolytic activity of an enzyme on small portions of beef, lamb, pork, or the like. A slurry prepared with different types of meats and other components may also be utilized for flavoring the foodstuff. The liquid protein extract may also be thickened by the addition of flours and the like.

In still another preferred embodiment, the method further comprises shredding the texturized foodstuff prior to its shaping and cutting.

The method of the invention may further comprise adding to the extruded foodstuff, prior to its shaping and cutting, or after the final product is formed, a nutritious and/or tasteful agent such as dried fruits, nuts, edible seeds, nuggets of dried meats and confections, among others.

The method of the present invention produces a versatile ready-to-eat vegetable or vegetable protein food which may be processed into a wide variety of shelf-stable food products, including treats simulating beef, pork, mutton, chicken, turkey, fish, and other seafoods. The end-product may be in the form of a paste, fiber, bar or stick, to be consumed directly or used as a meat substitute in conventional recipes. One embodiment of the product of the invention is a beef-type bar which, with proper packaging, may be sold at newsstands and vending machines and will make beef-flavored foods readily available to impulse buyers.

The vegetable or vegetable/animal protein product may be incorporated into the diet of people who require calorie-controlled meals and nutritious snack foods. In addition, the ready-to-eat food product described herein is also suitable for feeding people who are unable to prepare their own meals. The present foodstuff may be used in conjunction with a medically recommended protein supplement diet. The present food product may also be utilized in high-stress situations such as rations for amateur expeditioners and for military field use, where high protein and caloric content meals are required. The extended shelf life of the present food product permits its stockpiling for disaster and famine relief, as well. The present is a low-cost product, which if necessary, may be shipped for immediate use in emergencies.

Since the water activity of the processed vegetable or vegetable/animal protein foodstuff of the invention is kept low by selected packaging, the shelf life of the product may be up to about 18 to 24 months, and sometimes even longer. The products of this invention may have a soft, chewy, crisp, striated texture and visually appealing characteristics which simulate animal meat.

In another preferred embodiment of the invention, the method further comprises
 preparing a dough;
 co-extruding the dough around a core of the intermediate moisture foodstuff of the invention; and
 cooking the extruded foodstuff.

In another embodiment, the method further comprises preparing a dough;
 shaping or pressing the dough into a sheet of a desired size and shape;
 pressing the foodstuff of the invention to a size similar to the dough sheet;
 cooking the dough sheet; and
 applying the cooked sheet to at least one side of the pressed foodstuff of the invention.

The preparation of a dough may be attained by any of numerous methods known in the art depending on whether it is desired that it have a soft, flexible, breakable or crusty texture once it is incorporated into the final product.

If continuously encrusted (co-extruded) around a center-filling of the soft-moist foodstuff of this invention, the product may be cut and baked on sheet pans or on a continuous belt oven to cook and dry the dough and give it a light brown outer color.

If a laminating process is used, the dough may be shaped and cut with commercially available machinery. The size and thickness of the dough may vary. For example, it may be formed into a narrow, long stick, a bar, a paste, loaves, or pies of round, square or rectangular shape. The thickness of the dough may also be varied taking into consideration the thickness of the foodstuff core.

The shaped, texturized foodstuff may be pressed, either manually or mechanically as is known in the art. In general, the size and shape of the foodstuff filler is similar to that of the dough. However, there may be instances when the foodstuff core may be fully covered on all sides by the crust and its size, therefore, will be smaller than that of the dough.

The application of the cooked sheet of dough to the foodstuff core may be done as is known in the art by either manual or mechanical means. The foodstuff core may be utilized to fill in an already-shaped, cooked dough provided with walls and a bottom, or by superposing layers of same or different thicknesses and similar lengths of the foodstuff layer(s) and crust(s). An artisan would know how to prepare the different forms and shapes of the foodstuff product of the invention.

Any of the products provided herein may be wrapped with a low oxygen, low moisture permeable material, and the wrapping may be sealed by methods known in the art. The outer wrapping may also be oxygen impermeable, and/or more than one layer of wrapping may be placed around the foodstuff product.

Some of the products provided herein contain no animal protein, some contain a mixture of animal and vegetable protein, and some also have a liquid extract of proteins such as in meat gravy, and the like.

The meat-flavored sticks, bars and other products provided herein may also be provided with other nutritious and/or tasty components such as dry fruits, nuts, seeds and the like for increasing the protein content, providing different texture to the product and/or flavor.

Other objects, features and advantages of the invention will become evident in light of the following detailed description of a preferred exemplary embodiment according to the present invention.

EXAMPLES

Low-Cost Beef Bar

EXAMPLE 1

Texturized Soy Flour-Beef Pieces

The formulation of the product was as follows.

TABLE 1

| Composition of Soy Flour-Beef Pieces | |
|---|---|
| 200/70 soy flour (Cargill, Inc.) | 88.40 lb |
| Beef (7% fat content) | 21.00 lb |
| Caramel color (Sethness Co. P-330) | .60 lb |
| Total | 110.00 lb |

Beef containing approximately 7% fat was passed through a 3/16 in. grinder plate and placed in a silent cutter or bowl chop. The caramel color was sprinkled over it, and the mixture was chopped until a coarse emulsion was formed. In a commercial operation a continuous emulsifier as used for preparing sausage meat, may be used for this purpose. The content of the bowl was added to the commercial defatted soy flour (purchased ground to pass a U.S. 200 (mesh) sieve) in an upright mixer (Hobart), and mixed until uniformly dispersed. A coarser meal/flour, as large as U.S. 60 mesh, may also be used.

The resulting material, at approximately 30% moisture, was passed through a Wenger TX-52 twin-screw extruder (Wenger Manufacturing Co., Sabetha, Kans.), with the screws, barrel and die configured for texturization of soybean protein as recommended by the manufacturer. The diameter of each barrel of the machine was 52 mm wide. The machine was operated at 350 rpm. with a feed rate of approximately 220 lb/hr, and the extruded product exited the extruder under a pressure of 750 psi. at the die plate and at 217° F. The product was cooled to approximately 90° F., and passed through a Comitrol Mill (Urschel Manufacturing Company, Valparaiso, Ind.) equipped with a 0.18 in. cutting head. The resulting brown product looked and smelled like pieces of shredded roast beef.

EXAMPLE 2

Enzyme-Liquified Beef Gravy 10.00 lb of hamburger-grade beef containing about 20% fat were passed through a 3/16 in. meat grinder plate and placed in a steam jacketed kettle. Exactly 0.005 llb (0.05%) of Papain 16,000 (Miles, Inc., Elkhart, Ind.) were added to the meat, and the mixture stirred while heating at 158° F. After the mixture ceased to liquefy, it was brought to boiling to inactivate the enzyme. The preparation was then homogenized in a one-gallon size Waring blender, remixed, weighed and brought back to the original weight of 10.00 lbs by addition of water to compensate for loss of moisture through evaporation.

EXAMPLE 3

Formulated Product

The formulation of the product was as follows.

TABLE 2

| Formulation of Product | |
|---|---|
| Beef gravy as prepared in Example 2 | 9.199 lb |
| Texturized soy flour-beef shreds as prepared in Example 1 | 7.825 lb |
| Sugar (sucrose) | 1.625 lb |
| Modified starch (American Maize Co. "Polar Gel C") | 1.500 lb |
| Dextrose | 1.250 lb |
| Sorbitol | 0.875 lb |
| Glycerol (glycerin) | 0.625 lb |
| Propylene glycol | 0.500 lb |
| Dry barbecue flavor | 0.500 lb |
| Salt | 0.375 lb |
| Refined cottonseed oil (Lou Ana Co.) | 0.245 lb |
| Dry onion powder | 0.150 lb |
| Citric acid | 0.125 lb |
| Caramel color (Sethness Co. P-330) | 0.090 lb |
| Garlic powder | 0.075 lb |
| Potassium sorbate | 0.038 lb |
| Refined cottonseed oil containing 10% each of tertiary butylhydroquinone) (TBHQ) (Eastman Chemical Products, Inc.) and butylated hydroxytoluene (BHT) | 0.003 lb |
| Total | 25.000 lb |

The potassium sorbate was dissolved in the propylene glycol. All ingredients were combined in a twin-sigma blade mixer (J. H. Day Company, Cincinnati, Ohio), and mixed under 10 in. (Hg, mercury) vacuum to deaerate the mixture. The mixture then was fed into a Wenger X-20 extruder, with barrel and screw configured to rapidly heat the product with minor shear. The product exited the extruder through a straight ⅜ in. pipe at 210° F. The product was pressed into sheets ⅜ in. thick, then cooled, and sliced into bars 4 in. by 1 3/16 in. The bars were placed in FreshPak 500 clear multi-laminate pouches (Koch Supplies, Inc., Kansas, Mo.), and sealed on a Multivac impulse-heated bar sealer under slight vacuum after evacuation to 850 mbar. and released with nitrogen.

After equilibration at room temperature for 7 days, the bars contained 25.0% water determined by the Karl Fischer procedure, and had an $A_w$ of 0.84 and a pH of 5.5. Each bar weighed approximately 2.68 oz., and the product had a highly acceptable roast beef-like flavor.

Microbiological analysis of the product showed a very low (270 colonies/g) aerobic plate count, less than 10 colonies/g yeast, mold and Staphylococcus aureus; less than 3 colonies/g Escherichia coli; and was negative to Salmonella.

Nutritionally-Balanced Beef Bar

EXAMPLE 4

Texturized Soy Protein Concentrate-Beef Shreds

The soy concentrate-beef product was prepared as follows.

TABLE 3

| Formulation of Soy-Beef Shreds | |
|---|---|
| Soy protein concentrate (Central Soya Co. Promosoy 100 (TM)) | 46.20 lb |
| Beef clod (7% fat) | 42.00 lb |
| Soy fiber (Protein Technologies, Inc. Fibrim (TM) | 11.20 lb |
| Caramel color (Sethness Co. P-330) | 0.60 lb |
| Total | 100.00 lb |

The extruder-texturized portion of this product was made with soy protein concentrate in order to avoid potential flatulence problems associated with soy flour. Commercial soy protein concentrate was purchased (ground to pass a U.S. 100 sieve). Refined commercial soy cotyledon fiber was purchased having a 75 wt % dietary fiber content or higher, and ground to pass a U.S. 100 sieve. Beef containing approximately 7% fat was passed through a 3/16 in. grinder plate and placed in a silent cutter or bowl chop. The caramel color was sprinkled over it and the mixture was chopped until a coarse emulsion formed. In a commercial operation, a continuous emulsifier as those used for preparing sausage meat may be used for this purpose.

The content of the bowl was added to the soy protein concentrate and fiber and mixed in an upright mixer (Hobart Manufacturing Company, Troy) until it was thoroughly dispersed. The material having approximately 35% moisture was passed through a Wenger TX-52 twin-screw extruder with screws, barrel and die configured for texturization of soy protein as recommended by the manufacturer. The machine ran at 350 rpm, with a feed rate of approximately 220 lb/hr, and the extruded product exited at 218° F. from the die plate at 750 psi. The product was cooled to approximately 90° F. and passed through a Comitrol Mill equipped with a 0.18 in. cutting head.

The resulting brown product looked and smelled like pieces of shredded roast beef.

EXAMPLE 5

Cracker Meal

In a nutritionally-balanced product, it is in general undesirable to have excessive amounts of protein. Since soy concentrate contains about 70 wt % protein on a dry weight basis whereas soy flour contains approximately 55 wt % protein, it is desirable to have an additional texturized low-protein material for formulating the composite bar. This may be accomplished by making an expanded, shredded cracker meal.

A cracker meal was prepared as follows.

TABLE 4

| Composition of Cracker Meal | |
| --- | --- |
| General purpose baker's flour | 91.60 lb |
| Water | 8.00 lb |
| Caramel color (Sethness Co. P-330) | 0.40 lb |
| Total | 100.00 lb |

A general purpose patent flour was mixed dry with the caramel color in an upright mixer (Hobart) The mixture was then fed dry into the throat of a Wenger TX-52 twin-screw extruder with screw, barrel and die configured for making puffed pellets. A stream of water was then fed into the extruder in order to moisten the flour. The ratio between the feed rate of flour-color mixture and water was 92:8 weight:weight. The flour was not pre-mixed with the water before extrusion to prevent formation of glutinous balls. The product was extruded at 215° F. from a pre-die pressure of 1,500 psi., with an extruder rpm of 380 and throughout of 154 lb/hr.

The product was then cooled and cut into aerated "cracker meal" shreds using a Comitrol Mill equipped with a 0.18 in. cutting head. After tray-drying at ambient conditions, the moisture content of the cracker meal was approximately 14%.

EXAMPLE 6

Fine-Ground Beef 10.00 lb of trimmed beef containing approximately 7 wt % fat was passed through a 3/16 in. meat grinder plate and placed in a silent cutter or bowl chop. It was then chopped until a coarse emulsion formed. In a commercial operation, a continuous emulsifier, as those used for preparing sausage meat may be used for this purpose.

EXAMPLE 7

Formulated Product

This product was prepared as follows.

TABLE 5

| Formulation | |
| --- | --- |
| Beef prepared as in Example 6 | 7.740 lb |
| Texturized soy concentrate-beef shreds as prepared in Example 5 | 7.720 lb |
| Brown cracker meal as prepared in Example 5 | 2.000 lb |
| Sugar (sucrose) | 1.750 lb |
| Sorbitol | 1.000 lb |
| Dextrose | 0.875 lb |
| Refined cottonseed oil (Lou Ana Co.) | 0.875 lb |
| Modified starch (American Maize Co. Polar Gel C (TM)) | 0.750 lb |
| Glycerol | 0.500 lb |
| Dry barbecue flavor | 0.500 lb |
| Propylene glycol | 0.375 lb |
| Salt | 0.375 lb |
| Caramel color (Sethness Co. P-330) | 0.150 lb |
| Dry onion powder | 0.150 lb |
| Citric acid | 0.075 lb |
| Lactic acid | 0.050 lb |
| Garlic powder | 0.075 lb |
| Potassium sorbate | 0.038 lb |
| Refined cottonseed oil containing 10% each of tertiary butylhydroquinone (TBHQ) (Eastman Chemical Products, Inc.) and butylated hydroxytoluene (BHT) | 0.002 lb |
| Total | 25.000 lb |

All ingredients were combined in a twin-sigma blade mixer (J. H. Day Company), and mixed under 10 in. (Hg) vacuum to deaerate the mixture. The mixture was then fed into a Wenger X-20 extruder with barrel and screw configured to rapidly heat the product with minor shear. The product exited the extruder through a straight ⅜ in. pipe at 210° F.

The product was pressed into ⅜ in. thick sheets, cooled, and sliced into bars 4 in. by 1 3/16 in. The bars were placed in FreshPak 500 multi-laminate clear pouches, and were sealed on a Multivac impulse-heated bar sealer under slight vacuum after evacuation to 850 mbar. vacuum and released with nitrogen.

After equilibration at room temperature for 7 days, the bars contained 27% water as determined by the Karl Fischer procedure, and had an $A_w$ of 0.84 and a pH of 5.4. Each bar weighed approximately 2.68 oz, and contained 18.0% protein, 7.6% fat, 11.8% dietary fiber, and approximately 210 calories. The product was soft and had a highly acceptable beef flavor.

Microbiological analyses of the product showed an aerobic plate count of 8,200 colonies/g, less than 10 colonies/g yeast, mold and S. aureus, less than 3 colonies/g E. coli, and were negative to Salmonella. After storage for one month at room temperature, the aerobic plate count was 400 colonies/g, with less than 10 colonies/g yeast, mold and S. aureus, less than 3 colonies/g E. coli, and was negative to Salmonella.

Vegetarian-Type Bar

EXAMPLE 8

Texturized Soy Protein Concentrate

A soy protein concentrate was prepared as follows.

TABLE 6

| Formulation of Soy Protein Concentrate | |
| --- | --- |
| Soy protein concentrate (Central Soya Co. Promosoy 100 (TM)) | 75.40 lb |
| Caramel color (Sethness Co. P-330) | 0.60 lb |
| Water | 24.00 lb |
| Total | 100.00 lb |

An extruder-texturized portion of this product was made with a soy protein concentrate in order to avoid potential flatulence problems associated with soy flour. Commercial soy protein concentrate was purchased already ground to pass a U.S. 100. The caramel color was dissolved in the water and mixed with the soy protein concentrate in an upright mixer (Hobart).

The resulting material having approximately 30% moisture was passed through a Wenger TX-52 twin-screw extruder with screws, barrel and die configured for texturization of soy protein as recommended by the manufacturer. The machine was run at 350 rpm, with a feed rate of approximately 220 lb/hr, and the extruded product exited at 217° F. from the die plate at 900 psi. The product was cooled to approximately 90 IF and passed through a Bauer Mill (W. C. Cantrell Company, Ft. Worth, Tex.), equipped with closely-set small devil's tooth plates. The resulting brown shredded product looked like dried pieces of roast beef.

EXAMPLE 9

Cracker Meal

The cracker meal was prepared as follows.

TABLE 7

| Composition of Cracker Meal | |
| --- | --- |
| General purpose baker's patent flour | 91.60 lb |
| Water | 8.00 lb |
| Sethness Co. P-330 caramel color | 0.40 lb |
| Total | 100.00 lb |

A general purpose patent flour was mixed dry with the caramel color in an upright mixer (Hobart), and was fed dry into the throat of a Wenger TX-52 twin-screw extruder with screw, barrel and die configuration for making puffed pellets. A stream of water was then fed into the extruder to moisten the flour. The ratio between the feed rate of flour-color mixture and water was 92:8 by weight. The flour was not premixed with the water before extrusion in order to prevent the formation of glutinous balls.

The product was extruded at 215° F. from a pre-die pressure of 1,500 psi at 380 rpm extruder speed, and 154 lbs/hr throughput. The product was cooled and cut into an aerated "cracker meal", using a Comitrol equipped with a 0.18 in. cutting head. After tray drying under ambient conditions, the moisture content of the cracker meal was approximately 14.

EXAMPLE 10

Manufacture of Bar

The formulation of the vegetarian-type bar was as follows.

TABLE 8

| Formulation of Vegetarian-type Bar | |
| --- | --- |
| Texturized soy protein concentrate prepared in Example 8 | 8.403 lb |
| Deionized water | 5.670 lb |
| Brown cracker meal prepared in Example 9 | 1.750 lb |
| Sugar (sucrose) | 1.750 lb |
| Refined cottonseed oil (Lou Ana Co.) | 1.750 lb |
| Modified starch (American Maize Co. Polar Gel C(TM)) | 1.500 lb |
| Sorbitol | 1.000 lb |
| Dextrose | 1.000 lb |
| Glycerol | 0.625 lb |
| Beef teriyaki flavor (Bell Flavor Labs.) | 0.500 lb |
| Propylene glycol | 0.375 lb |
| Salt | 0.187 lb |
| Dry onion powder | 0.150 lb |
| Citric acid | 0.125 lb |
| Caramel color (Sethness Co. P-330) | 0.100 lb |
| Garlic powder | 0.075 lb |
| Potassium sorbate | 0.038 lb |
| Refined cottonseed oil containing 10% each of tertiary butylhydroquinone (TBHQ) (Eastman Chemical Products, Inc.) and butylated hydroxytoluene (BHT) | 0.002 lb |
| Total | 25.000 lb |

The potassium sorbate was dissolved in the propylene glycol. All ingredients were combined in a mixer (J. H. Day Company twin-sigma blade mixer), and mixed under 10 in. (Hg) vacuum to deaerate the mixture. The mixture then was fed into a Wenger Manufacturing Company X-20 extruder, with barrel and screw configured to rapidly heat the product with minor shear. The product exited the extruder through a straight ⅜ in. pipe at 210° F. and was pressed into ⅝ in. thick sheets, cooled, and sliced into bars 4×1 3/16 in. The bars were placed in FreshPak 500 (Koch Supplies, Inc., Kansas City, Mo.) multi-laminate clear plastic pouches, and were sealed on an impulse-heated bar sealer (Multivac) under slight vacuum after evacuation to 850 mbar. vacuum and released with nitrogen.

After equilibrating at room temperature for 7 days, the bars contained 30% water determined by the Karl Fischer procedure, and had an $A_w$ of 0.85 and a pH of 5.3. Each bar weighed approximately 2.68 oz, and contained 14% protein and 8.8% fat. The bar had a soft texture and beef-like flavor.

Initial microbiological analyses of the product showed an aerobic plate count of 9,100 colonies/g, less than 10 colonies/g yeast, mold and S. aureus; less than 3 colonies/g *E. coli*, and were negative to Salmonella.

Fruit Newton-Type Product

EXAMPLE 11

Making a Crust

A crust was prepared as follows.

TABLE 9

| Composition of Crust Mix | |
| --- | --- |
| Bleached cake flour | 5.610 lb |
| Granulated sugar (sucrose) | 1.085 lb |
| Water for processing | 1.078 lb |
| All-cottonseed liquid shortening (Lou Ana Foods Co.) | 0.995 lb |
| Corn syrup solids (American Maize Co. Frodex 55) | 0.543 lb |
| Corn syrup (Archer Daniel Midland 42DE/43 Be') | 0.271 lb |
| Non-fat dry milk solids (Carnation Co.) | 0.271 lb |
| Sodium bicarbonate (Stauffer Co.) | 0.027 lb |
| Sodium aluminum phosphate (Stauffer Co. Actif 8(TM)) | 0.027 lb |
| Salt (Morton Salt Co.) | 0.045 lb |
| Soybean lecithin (Central Soya Co. Centrophase HR-2B (TM)) | 0.023 lb |
| Lemon oil U.S.P. (Otteris Mfg. Co.) | 0.005 lb |
| Annatto color (Miles Inc. AFC WOS) | 0.0015 lb |
| Potassium sorbate | 0.0135 lb |
| Refined cottonseed oil containing 10% each of tertiary butylhydroquinone (TBHQ) (Eastman Chemical Products, Inc.) and butylated hydroxytoluene (BHT) | 0.005 lb |
| Total | 10.000 lb |

The shortening was creamed with the sugar and the annatto color and lecithin in an upright mixer (Hobart), followed by addition of the remaining ingredients except for flour and water. The flour was added, with mixing continued until well-dispersed, and then water was added in two steps and dispersed. The dough was rolled into sheets approximately 1/16 in. thick and was baked on thin cookie sheets at 350° F. for approximately 12–15 min. until done. The sheets of crust, approximately ⅛ in. thick, were then cooled, removed from the baking sheets and stored until used. This procedure was used to make crusts for the fruit newton-like product, although in commercial practice a dough with formula adjusted for good machining would be mechanically engrossed around an extruded bar of filling, and would be baked in a continuous band oven.

EXAMPLE 12

Texturized Soy Protein Concentrate-Beef Fibers

The fibers were prepared as follows.

TABLE 10

| Fiber Composition | |
| --- | --- |
| Soy protein concentrate (Central Soya Co. Promosoy 100 (TM)) | 58.00 lb |
| Beef clod (7% fat) | 41.40 lb |

TABLE 10-continued

| Fiber Composition | |
|---|---|
| Caramel color (Sethness Co. P-330) | 0.60 lb |
| Total | 100.00 lb |

An extruder-texturized portion of this product was made with soy protein concentrate in order to avoid potential flatulence problems associated with soy flour. Commercial soy protein concentrate was purchased (ground to pass a U.S. 100 sieve). Beef, containing approximately 7% fat, was passed through a 3/16 in. grinder plate and placed in a silent cutter ("bowl chop"). The caramel color was sprinkled over it and the mixture was chopped until a coarse emulsion was formed. It is realized that in a commercial operation a continuous emulsifier as used for preparing sausage meat might be used. The contents of the bowl were added to the soy protein concentrate and was mixed in an upright mixer (Hobart) until dispersed The material, at approximately 35% moisture, was passed through a Wenger TX-52 twin-screw extruder, with the screws, barrel and die configured for texturization of soy protein as recommended by the manufacturer. The machine ran at 350 rpm, with a feed rate of approximately 220 lb/hr, and the extruded product exited at 218° F. from the die plate at 750 psi. The product was cooled to approximately 900° F. and passed through a Comitrol equipped with a 0.18 in. cutting head. The resulting brown product looked and smelled like pieces of shredded roast beef.

EXAMPLE 13

Enzyme-Liquified Gravy 10.00 lb of trimmed beef, containing approximately 7% fat, was passed through a 3/16 in. meat grinder plate and was placed in a steam jacketed kettle. Exactly 0.005 lb (0.05%) of Papain 16,000 was added to the meat, and the mixture stirred while heating to 158° F. After the mixture no longer liquefied, it was brought to boiling to inactivate the enzyme. It was then homogenized in a one-gallon size Waring blender, remixed, weighed and brought back to the original weight of 10.00 lbs by addition of water to compensate for loss due to evaporation.

EXAMPLE 14

Formulated Product with Crust

The product was manufactured as follows.

TABLE 12

| Product Composition | |
|---|---|
| Beef gravy as prepared in Example 13 | 7.500 lb |
| Texturized soy concentrate-beef shreds as prepared in Example 12 | 7.052 lb |
| Dark raisins, ground through ⅛ in plate | 2.500 lb |
| Dextrose | 1.250 lb |
| Corn syrup (Archer Daniel Midland Co. 42/43) | 1.625 lb |
| Sorbitol | 1.000 lb |
| Propylene glycol | 0.837 lb |
| Brown sugar | 0.750 lb |
| Refined cottonseed oil (Lou Ana Co.) | 0.750 lb |
| Modified starch (American Maize Co. Polar Gel C(TM)) | 0.750 lb |
| Glycerol | 0.500 lb |
| Salt | 0.250 lb |
| Citric acid | 0.125 lb |
| Caramel color (Sethness Co. P-330) | 0.063 lb |
| Potassium sorbate | 0.038 lb |

TABLE 12-continued

| Product Composition | |
|---|---|
| Orange oil (Sunkist Growers, Inc., California) | 0.008 lb |
| | 0.002 lb |
| Refined cottonseed oil containing 10% each of tertiary butylhydroquinone (TBHQ) (Eastman Chemical Products, Inc.) and butylated hydroxytoluene (BHT) | |
| Total | 25.000 lb |

All ingredients were combined in a twin-sigma blade mixer (J. H. Day Company), and mixed under 10 in. (Hg) vacuum to deaerate the mixture. The mixture then was fed into a Wenger X-20 extruder, with barrel and screw configured to rapidly heat the product with minor shear. Product exited the extruder through a straight ⅜ in. pipe at 210° F. The product was pressed into sheets ¼ in., cooled, and the crusts were applied to both sides. The products were allowed to temper together approximately 18 hrs until the crusts lost their brittleness and were sliced into bars 2⅛ in. by 2⅛ in. The assembled bars were approximately ½ in. thick. The bars were placed in FreshPak 500 multi-laminate clear pouches, and were sealed on a Multivac impulse-heated bar sealer under slight vacuum after evacuation to 850 mbar. and release with nitrogen.

After equilibrating at room temperature for 7 days, the bars contained 20.9% water determined by the Karl Fischer procedure, and had an $A_w$ of 0.78 and a pH of 5.6 for the macerated product, an $A_w$ of 0.78 and pH of 6.4 for the crust and an $A_w$ of 0.79 and pH of 5.0 for the filling. Each bar weighed approximately 1.68 oz., and contained 14.3% protein and 9.3% fat. The product was soft and had a highly acceptable beef and fruit flavor.

Microbiological analyses of the product showed a very low aerobic plate count of 160/g, 100 colonies/g mold count; less than 10 colonies/g yeast and S. aureus, less than 3 colonies/g E. coli, and were negative to Salmonella.

Beef, Fruit and Nut Jerky-Type Product

EXAMPLE 15

Texturized Red Soy Concentrate-Beef Fibers

The fibers were prepared as follows.

TABLE 13

| Composition of Fibers | |
|---|---|
| Soy Protein concentrate (Central Soya Co. Promosoy 100 (TM)) | 58.00 lb |
| Beef clod (7% fat) | 41.60 lb |
| Red alumina lake (Colorcon, Inc. No. 40) | 0.40 lb |
| Total | 100.00 lb |

The extruder-texturized portion of this product was made with soy protein concentrate in order to avoid potential flatulence problems associated with soy flour. Commercial soy protein concentrate was purchased (ground to pass a U.S. 100 sieve). Beef, containing approximately 7% fat, was passed through a 3/16 in. grinder plate and placed in a silent cutter ("bowl chop"). The red color was dusted over it, and the mixture was chopped until a coarse emulsion was formed. It is realized that in a commercial operation a continuous emulsifier as used for preparing sausage meat might be used. The contents of the bowl were added to the soy protein concentrate and mixed in an upright mixer (Hobart) until dispersed. The material, at approximately 35% moisture, was passed through a Wenger TX-52 twin-screw extruder, with the screws, barrel and die configured for texturization of soy protein as recommended by the manufacturer. The machine ran at 3 50 rpm, with a feed rate of approximately 220 lb/hr. The product exited the die of the extruder at 218° F. and 750 psi. The product was cooled to approximately 90° F. and passed through a Comitrol equipped with a 0.18 in. cutting head. The resulting red product looked like pieces of shredded corned beef.

EXAMPLE 16

Enzyme-Liquified Gravy

A liquefied gravy was prepared as follows. 10.00 lb of trimmed beef containing approximately 7% fat were was passed through a 3/16 in. meat grinder plate and placed in a steam jacketed kettle. Exactly 0.005 lb of Papain 16,000 (0.05%) were added to the meat, and the mixture stirred while heating at 158° F. After the mixture no longer liquefied, it was brought to boiling to inactivate the enzyme. The mixture was then homogenized in a one-gallon size Waring Blender, remixed, weighed and brought back to the original weight of 10.00 lbs by addition of water to compensate for water loss due to evaporation.

EXAMPLE 17

Binder Syrup

A syrup was prepared as follows.

TABLE 15

| Binder Syrup Composition | |
|---|---|
| Beef gravy as prepared in Example 16 | 5.122 lb |
| Modified starch (American Maize Co. Polar Gel C(TM)) | 1.136 lb |
| Brown sugar | 0.500 lb |
| Corn syrup solids (American Maize Co. Frodex 55) | 0.500 lb |
| Smoked barbecue flavor | 0.500 lb |
| Glucose | 0.450 lb |
| Propylene glycol | 0.425 lb |
| Sorbitol - 70% syrup | 0.425 lb |
| Glycerol | 0.300 lb |
| Refined cottonseed oil (Lou Ana Foods Co.) | 0.300 lb |
| Salt (Morton Salt Co.) | 0.250 lb |
| Citric acid | 0.060 lb |
| Potassium sorbate | 0.030 lb |
| Refined cottonseed oil containing 10% each of tertiary butylhydroquinone (TBHQ) (Eastman Chemical Products, Inc.) and butylated hydroxytoluene (BHT) | 0.002 lb |
| Total | 10.000 lb |

The potassium sorbate was dissolved in the propylene glycol. All ingredients were then combined in an upright mixer (Hobart), and heated to 200° F.

EXAMPLE 18

The Bar

The bar as prepared as follows.

TABLE 16

| Bar Formulation | |
|---|---|
| Red texturized soy protein concentrate-beef fibers as prepared in Example 15 | 3.40 lb |
| Diced apricots | 0.60 lb |
| Golden raisins | 0.60 lb |
| Dried currants or small dark raisins | 0.60 lb |
| Sliced almonds | 0.60 lb |

TABLE 16-continued

| Bar Formulation | |
|---|---|
| Binder syrup as prepared in Example 17 | 4.20 lb |
| Total | 10.00 lb |

The dried fruits were dipped in a 5% solution of potassium sorbate dissolved in a 0.80 $A_w$ solution of glycerine and water, mixed to ensure complete wetting of the surfaces, and allowed to drain. The components described above, except for the fruit, were added to an upright mixer bowl (Hobart) and where completely mixed. The potassium sorbate solution-treated fruit was then folded in with minimum mixing to limit breakage. The product was pressed into 5/8 in. thick sheets, cooled, and cut into strips 4×1 3/16 in. The bars were placed in FreshPak multi-laminate clear pouches, and sealed on an impulse-heated bar sealer (Multivac) under slight vacuum after evacuation to 850 mbar. and released with nitrogen.

After equilibrating at room temperature for 7 days, the bars contained 24.9% water determined by the Karl Fischer procedure, an $A_w$ of 0.80 and a pH of 5.7. The bars weighed approximately 1.0 oz. and had a tangy smoke-cured meat flavor.

Microbiological analyses of the product showed an aerobic plate count of 70 colonies/g, less than 10 colonies/g yeast, mold and S. aureus, less than 3 colonies/g E. coli, and were negative to Salmonella.

The invention being described in conjunction with the foregoing specific embodiments, many alternatives, variations and modifications will be apparent to those of ordinary skill in the art. Those alternatives, variations and modifications are intended to fall within the spirit and scope of the appended claims.

We claim:

1. A method of preparing a ready to eat, intermediate moisture, texturized foodstuff for human consumption, comprising:

admixing ingredients consisting essentially of i) a dehulled, oilseed protein in a form selected from the group consisting of meal, flour, concentrate and isolate, and ii) a first source of water selected from a group consisting of water, slid meat products, a liquid meat digest, a liquid meat extract, liquid milk products, cheese whey, diluted cereal grain extract, and fermented beer to obtain a first mixture having a moisture content of about 25 to 50 wt. %.

cooking, working and extruding said first mixture at a temperature of about 212° to 350° F. and an exit pressure of about 200 to 2000 psi to produce a first texturized foodstuff having a fibrous meat-like texture;

grinding said first texturized foodstuff to produce shreds;

admixing said shredded first texturized foodstuff and a second source of water to obtain a second mixture;

extrusion cooking and pasteurizing said second mixture at a temperature above about 190° F.;

decreasing the temperature of said pasteurized second mixture to about ambient temperature to produce a second texturized foodstuff; and shaping and cutting said second texturized foodstuff to a desired shape and size.

2. The method of claim 1, wherein the second source of water is selected from the group consisting of water, solid meat products, a liquid meat digest or extract, vegetable flour dough, liquid milk products, cheese whey, diluted cereal grain extract, fermented beer, fresh fruits, cooked fruits, fresh vegetables and cooked vegetables.

3. The method of claim 1, wherein
said first water source is solely meat; and the method further comprises:
size reducing said meat into pieces prior to admixing said meat with said dehulled oilseed protein.

4. The method of claim 1, further comprising
adding to said shredded first texturized foodstuff, before admixing said shredded first texturized foodstuff with said second source of water, at least one additive selected from the group consisting of coloring, antimicrobial preservatives, antioxidants, anti-browning agents, seasonings, emulsifiers, sweeteners, salts, liquid or solidified oils, edible acids, humectants, fillers and bulk agents; and
dispersing the additive in said shredded first texturized foodstuff.

5. The method of claim 1, further comprising
adding to said second texturized foodstuff, before said shaping and cutting step, a nutritious agent selected from the group consisting of dried fruits, nuts, seeds, and dried meat pieces.

6. The method of claim 1, further comprising
preparing a dough;
shaping and cutting said dough into a sheet of a desired size and thickness;
cooking said dough sheet;
pressing the shaped and cut second texturized foodstuff to a size similar to or smaller than that of said dough sheet; and
applying said cooked dough sheet to at least one side of said shaped and cut second texturized foodstuff.

7. The method of claim 1, further comprising
wrapping said shaped and cut second texturized foodstuff with a low oxygen and moisture permeable material; and
sealing said material wrapped around said second texturized foodstuff.

8. The method of claim 1,
wherein said second source of water is selected from the group consisting of comminuted meat, liquid meat extract, and liquid meat digest, and
wherein, in said second texturized foodstuff, said shredded first texturized foodstuff and said second source of water are in a proportion of about 15 to 40 wt. % of said first texturized foodstuff to about 20 to 50 wt. % of said second source of water.

9. The method of claim 8, wherein
said liquid meat extract comprises an animal meat concentrate.

10. The method of claim 9, wherein said animal meat concentrate is prepared by
digesting animal meat with a proteolytic enzyme; and
homogenizing said digested animal meat.

* * * * *